(12) United States Patent
Szardenings et al.

(10) Patent No.: US 9,193,986 B2
(45) Date of Patent: Nov. 24, 2015

(54) METHOD FOR MARKING OR IMMOBILISING A TARGET STRUCTURE

(71) Applicant: Fraunhofer-Gesellschaft Zur Forderung Der Angewandten Forschung e.V., Munich (DE)

(72) Inventors: Michael Szardenings, Wolfenbüttel (DE); Ingo Grunwald, Lilienthal (DE); Klaus Rischka, Tostedt (DE); Katharina Richter, Bremen (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/026,022

(22) Filed: Sep. 13, 2013

(65) Prior Publication Data

US 2014/0162303 A1 Jun. 12, 2014

Related U.S. Application Data

(60) Provisional application No. 61/701,133, filed on Sep. 14, 2012.

(30) Foreign Application Priority Data

Sep. 13, 2012 (DE) .................. 10 2012 216 346

(51) Int. Cl.
*C12Q 1/26* (2006.01)
*G01N 33/533* (2006.01)
*A61K 47/48* (2006.01)

(52) U.S. Cl.
CPC ............ *C12Q 1/26* (2013.01); *A61K 47/48038* (2013.01); *G01N 33/533* (2013.01)

(58) Field of Classification Search
CPC .................................................. G01N 33/533
USPC ........................................................ 436/140
See application file for complete search history.

(56) References Cited

FOREIGN PATENT DOCUMENTS

| WO | WO 99/36465 | 7/1999 |
| WO | WO 2011/153250 | 12/2011 |
| WO | WO 2012/060544 | 5/2012 |

OTHER PUBLICATIONS

Umanah et al. "Identification of residue-to-residue contact between a peptide ligand and its G protein-coupled receptor using periodate-mediated dihydroxyphenylalanine cross-linking and mass spectrometry", JBC, 2010,285(50):39425-39436.*
Riedel et al. "Megalin-dependent yellow endocytosis restricts melanization in the Drosophila cuticle", Development, 2011,138:149-158.*
Umanah et al. "Cross-linking of a DOPA-containing peptide ligand into its G protein-coupled receptor", Biochemistry, 2009, 48:2033-2044.*
Figueroa-Espinoza et al. J. Agric. Food Chem., 1999, 47:497-503.*
Nickoloff, Brian J. et al., "Affinity-Dependent Cross-Linking to Neurotoxin Sites of the Acetylcholine Receptor Mediated by Catechol Oxidation," Biochemistry, American Chemical Society, vol. 24, No. 4, 1985.
Gallop, Paul M. et al., "Is the Antioxidant, Anti-Inflammatory Putative New Vitamin, PQQ, Involved With Nitric Oxide in Bone Metabolism?" Connective Tissue Research, 1993, vol. 29, pp. 153-161.
Madhavi, Vernekar et al., "Laccase: Properties and Applications," BioResources 4(4), 2009, pp. 1694-1717.
Nonaka H. et al., "Selective covalent labeling of tag-fused GPCR proteins on live cell surface with a synthetic probe for their functional analysis." J Am Chem Soc. Jul. 14, 2010; 132(27): 9301-9 (Abstract).
Hwang DS, et al., "Cell adhesion biomaterial based on mussel adhesive protein fused with RGD peptide." Biomaterials. Oct. 2007; 28(28): 4039-46. (Abstract).
Richter K., Peptidinspiriete Materialentwicklung. Dissertation, Bremen 2012 (http://elib.suub.uni-bremen.de/edocs/00102824-1.pdf; recherchiert am Jun. 9, 2013).

* cited by examiner

*Primary Examiner* — Bin Shen
(74) *Attorney, Agent, or Firm* — Preti Flaherty Beliveau & Pachios LLP (57) ABSTRACT

Method for marking a target structure, comprising the following steps:
 a) providing a compound V that includes at least one dihydroxy- or trihydroxyphenyl group,
 b) providing a means for converting the dihydroxy- or trihydroxyphenyl group to a quinone group,
 c) providing a target structure,
 d) oxidizing the dihydroxy- or trihydroxyphenyl group of the compound V to the quinone group, and
 e) contacting the compound V with the target structure, so that a covalent bond can be formed,
 wherein
  in step e) the compound V is used in a concentration such that the maximum concentration of dihydroxy-, trihydroxyphenyl groups and quinone groups that are introduced by the compound V is ≤500 μM, preferably ≤300 μM, and more preferably ≤100 μM.

14 Claims, 8 Drawing Sheets

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: polypeptide for marking
<220> FEATURE:
<221> NAME/KEY: Ac
<222> LOCATION: (1)..(1)
<223> OTHER INFORMATION: Xaa in position 1 is any amino acid and is an
      "Ac"-residue
<220> FEATURE:
<221> NAME/KEY: lysine with attached chromophore
<222> LOCATION: (13)..(13)
<223> OTHER INFORMATION: Xaa in position 13 is amino acid lysine with
      attached FITC: chromophore, fluorescein, excitation wavelength 490
      nm, emission wavelength 520 nm
<220> FEATURE:
<221> NAME/KEY: DOPA
<222> LOCATION: (16)..(16)
<223> OTHER INFORMATION: Xaa in position 16 is any amino acid and
```

```
         defines DOPA

<400> SEQUENCE: 1

Xaa Ser Pro Arg Gly Asp Leu Ala Val Leu Gly His Xaa Gly Gly Xaa
1               5                   10                  15

Gly
```

METHOD FOR MARKING OR IMMOBILISING A TARGET STRUCTURE

The invention relates to a method for marking a target structure, wherein a compound V containing a dihydroxy- or trihydroxyphenyl group is covalently bonded to a target structure by oxidation of this group to the quinone. In this connection the concentration conditions of the compound containing the dihydroxy- or trihydroxyphenyl group are adjusted in such a way that only quite a small proportion of the quinone groups react with one another so that a dimerisation or polymerisation occurs.

The invention also relates to the use of a compound V for marking a target structure, wherein an oxidation of the dihydroxy- or trihydroxyphenyl group takes place (preferably via an enzyme).

In a large number of marking methods known in the prior art for biological structures, in particular for cells, the marking is carried out for example by probes, often without a covalent bond being formed between the marking and the to be marked construct. In order that the bond between the marking and the to be marked construct remains stable for a sufficiently long time, so that for example measurements can be carried out or biochemical or biological reactions can take place, as a rule affinities with dissociation constants in the sub-nanomolar range are necessary, which have half-lives of the formed complex in the region of at least several minutes. As a rule only antibodies have such an affinity and accordingly they are the preferred reagents for methods such as for example the marking or sorting of cells. Although many other possible molecules for marking, such as for example peptides, have a similarly high specificity for the binding partner to be marked, the binding constants and therefore the half-life of a formed complex are however not sufficient for most methods. This means that the binding equilibrium compared with covalent bonds is displaced more strongly in the direction of the non-bound partners. As a result higher marking structure concentrations have to be used in order to achieve a desired marking result. This also leads to an increased background signal. In the formation of an (irreversible) covalent bond between the binding partners the stability of the complex in principle no longer plays a role in the success of the execution of marking experiments, since it is possible to separate the non-bound remaining part of the marking molecules without adversely affecting the signal strength of the marking reaction.

A gentle covalent marking of molecules, in particular of cell surface markers in vitro and in vivo, is according to the present state of the art only possible with chemically activated and mostly unstable marking probes.

For this purpose it is generally normal practice to produce reactive functional groups. In addition however several steps have to be carried out for example in the activation of carboxylic acids with EDC/NHS. In particular the activated carboxylic acid generally has to be purified to remove the reagents, a procedure in which the unstable activated group also decomposes further (Review: Hackenberger C P, Schwarzer D. (2008): "Chemoselective ligation and modification strategies for peptides and proteins". Angew Chem Int Ed Engl. 2008; 47(52): 10030-74).

Another alternative is the so-called click chemistry, in which again two molecules can be covalently coupled to one another also under physiological conditions. This method presupposes however that both molecules being coupled have been modified beforehand. The modification of both molecules is however significantly more complicated than in the case of the invention described here, and in many cases is even impossible. The advantage of this method, which is also highly acknowledged in specialist circles, is however the stability of the starting compounds and the very rapid and highly specific reaction, which means that in the case of the invention described here only at least one precisely definable reactant is involved in the reaction. The reaction of the partners in many cases also does not presuppose the structure of a binding molecule specified here, and is therefore unsuitable for example for determining concentrations of unknown amounts of the object to be marked. (Review: Sletten E M, Bertozzi C R.: "Bioorthogonal chemistry: fishing for selectivity in a sea of functionality." Angew Chem Int Ed Engl. 2009; 48(3(:6974-98).

From the prior art it is also known that, for example, the bivalve *Mytilus edulis* is able with the aid of proteinogenic byssus threads and adhesive plaques to adhere to a large number of surfaces. These surfaces include glass, metal, wood, plastic and even Teflon. The adhesive consists of different proteins, which are identified as Mefp (*Mytilus edulis* food proteins). Mefp-1 is an essential constituent of the outer coating of the byssus and plaques. The composition of this protein is remarkable. The protein is a repeating decapeptide with a molecular weight of 108 kDa. Mefp-3 and Mefp-5 are responsible for the actual adhesive process. These proteins are localised in the boundary layer at the substrate surfaces. Mefp-2 is responsible for the foam-like morphology and the stabilisation of the adhesive. The collagen fibres of the byssus are bound by Mefp-4 to the plaque proteins. Particularly noteworthy is the DOPA fraction in the adhesive (10 to 27 mol-%).

DOPA is, due to its multifarious reaction possibilities, a key amino acid of the mussel adhesive both for adhesion and also cohesion. A decisive factor for the cohesion are covalent cross-linkages, which are established on the one hand by the so-called with amino groups in the lysine side chains and also by the bonding of a Schiff's base (imine) and inter alia by the free-radical dimerisation of the catechol residues via the intermediate stage of a quinone. The catechol subunit of DOPA is furthermore able to form extremely stable metal complexes, which likewise contribute significantly to the stabilisation of the adhesive. The cross-linking reactions can be initiated enzymatically by the addition of for example a tyrosinase or laccase as well as by oxidising agents such as $NaIO_4$ or $H_2O_2$.

Scheme 1

The problem with these adhesion phenomena known from nature is that a large number of secondary reactions and polymerisation reactions are not only possible, but also actually take place (cf. Scheme 1). For this reason the system has hitherto not been sufficiently manageable for the specific marking of target structures. The use in relevant measurement technology methods, in which for regulatory reasons the conditions of the reaction and the employed molecules have to be precisely defined, was therefore not feasible in the specialist field. These also include for example the methods of medical diagnosis, medical technology and medical transplant methods regulated by corresponding ISO standards.

Against this background the object of the present invention was to provide a method with which additional marking methods apart from those known in the prior art can be used for in particular biological target structures. In addition the method should preferably be able to be designed to be so gentle that even intact cells can be marked without any loss of integrity.

SUMMARY OF THE INVENTION

According to the invention this object is achieved by a method for marking a cell structure, comprising the following steps:
a) providing a compound V that includes at least one dihydroxy- or trihydroxyphenyl group,
b) providing a means for converting the dihydroxy- or trihydroxyphenyl group to a quinone group,
c) providing a target structure,
d) oxidising the dihydroxy- or trihydroxyphenyl group of the compound V to the quinone group, and
e) contacting the compound V with the target structure, so that a covalent bond can be formed,
wherein
in step e) the compound V is used in a concentration such that the maximum concentration of dihydroxy-, trihydroxyphenyl groups and quinone groups that were introduced by the compound V is ≤500 µM, preferably ≤300 µM, and more preferably ≤100 µM. In this connection it is preferred—if dihydroxy-, trihydroxyphenyl and/or quinone groups are simultaneously present—that the aforementioned concentrations are the sum of the individual concentrations of the aforementioned groups.

DESCRIPTION OF THE DRAWING

The present invention is described in detail below in conjunction with the drawing of which.

DETAILED DESCRIPTION OF THE INVENTION

According to the invention this object is achieved by a method for marking a cell structure, comprising the following steps:
a) providing a compound V that includes at least one dihydroxy- or trihydroxyphenyl group,
b) providing a means for converting the dihydroxy- or trihydroxyphenyl group to a quinone group,
c) providing a target structure,
d) oxidising the dihydroxy- or trihydroxyphenyl group of the compound V to the quinone group, and
e) contacting the compound V with the target structure, so that a covalent bond can be formed,
wherein
in step e) the compound V is used in a concentration such that the maximum concentration of dihydroxy-, trihydroxyphenyl groups and quinone groups that were introduced by the compound V is ≤500 µM, preferably ≤300 µM, and more preferably ≤100 µM. In this connection it is preferred—if dihydroxy-, trihydroxyphenyl and/or quinone groups are simultaneously present—that the aforementioned concentrations are the sum of the individual concentrations of the aforementioned groups.

Marking in the sense of the present invention is understood to mean a specific binding of a compound (here compound V) to a target structure via specific recognition sequences. In this connection specific recognition sequences are those that, on account of their spatial structure, have an enhanced affinity for the target structure or for structures on the surface of the target structure. Preferred specific recognition sequences are in this connection DNA sequences, RNA sequences and amino acid sequences.

The term "providing" in the sense of the present invention is understood to mean any form of making available. In particular, and especially for many cases, a provision involving an in situ production of the compound to be provided is also preferred.

Surprisingly it has been found that with the method according to the invention, by means of an adequate monitoring of the concentration of the compound V—either as concentration in the solution or as concentration on the surface on which it is to be
immobilised—good and reproducible results in the binding to the cell structure can be achieved without uncontrolled secondary reactions occurring to an undesirable extent, in particular dimerisations and polymerisations of dihydroxy- or trihydroxyphenyl groups oxidised to quinones.

Preferably an enzyme for converting the dihydroxy- or trihydroxyphenyl group to a quinone group is an oxidoreductase (EC 1 according to the classification of IntEnz (Integrated relational Enzyme database of the Swiss Institute of Bioinformatics (SIB)).

It is furthermore preferred if the enzyme for converting the dihydroxy- or trihydroxyphenyl group to a quinone group is selected from the group consisting of the enzyme classes according to the abovementioned classification EC 1.10 (oxidoreductases that act on diphenols and similar substances as donors) and EC 1.14 (oxidoreductases that act on paired donors with incorporation or reduction of molecular oxygen).

Particularly preferably the oxidoreductase is selected from the group EC 1.10.3 (with oxygen as acceptor) and EC 1.14.18 (with another compound as donor and with incorporation of an oxygen atom) and most particularly preferably an oxidoreductase is selected from the classes EC 1.10.3.2 (laccases) and EC 1.14.18.1 (monophenol monooxigenase). Laccases are preferred most of all.

It has surprisingly been found that the binding rate of the quinone (as a rule formed by oxidation) matches very well normal binding rates of specific sequences to their target structures: accordingly it is also possible in practice to as it were "freeze in" a highly reversible binding event to the target structure. This means that the equilibrium due to the covalent bonds via the quinone, which quickly follow the specific non-covalent bonding, is significantly displaced to target structure/binding structure complexes. In addition there is also the fact that the activation can take place via enzymes under relatively mild conditions (particularly in the case of the preferred enzymes), so that also complex target structures, such as for example cells, can be reliably, and in the case of marking, specifically bound without any loss of their functional capability.

With the method according to the invention it is in particular also possible to add the activating enzymes to the solution that also contains the potential target structures.

As already indicated above, the covalent bond via the quinone is formed in particular via coupling to amino or thio groups that are normally present in (biological) target structures.

A method according to the invention is preferred in which the at least one dihydroxy- or trihydroxyphenyl group is a constituent of DOPA, dopamine, caffeic acid or a corresponding bound group from one of these compounds (in other words, DOPA, dopamine or caffeic acid are bonded as residue to a molecule).

Obviously the person skilled in the art understands that the preferred constituents carrying the dihydroxy group can also be corresponding residues. Likewise it is obvious that the constituents carrying corresponding dihydroxy group can also be produced in situ, for example by oxidation of a tyrosine residue. In practise particularly effective markings have been successfully achieved with the preferred catechol group-carrying structures.

Also preferred in the context of the invention is a method in which the compound V contains exactly one dihydroxy- or trihydroxyphenyl group.

This has the advantage that also the absolute concentration of the catechol groups that are available (including trihydroxyphenyl groups) can thus easily be monitored via the absolute concentration of the structures V.

According to the invention a method is preferred in which the compound V additionally has binding properties for the target structure or parts of the target structure, preferably in the form of a specific binding domain.

Preferred in the context of the present specification are "specific binding properties" such that the compound V in the presence of the specific binding properties binds with a probability increased by a factor of at least 10 (preferably under normal conditions) to a specific region of the target structure, compared to other regions of the target structure.

Also preferred are these properties in the form of a specific binding domain, i.e. a region as part of the compound V, which on account of its spatial structure has an increased affinity for a specific region of the target structure or for structures on the surface of the target structure. The binding domain increases the probability of binding to the target structure by at least a factor of 10 compared to the same compound V without this binding domain. Most particularly preferably the bond formed on account of the specific binding properties or specific binding domain is a non-covalent bond.

The following for example may be such a specific binding domain: receptor ligands (any type), peptide sequences, carbohydrates, antibodies, RNA sequences, DNA sequences, antibody fragments, enzyme substrates, enzyme inhibitors or effectors, and also binding peptide or protein fragments from phage display selections.

Corresponding to what has been said above, a method according to the invention is preferred in which the specific binding properties, in particular the specific binding domain for the non-covalent bond, are directed to the target structure. In this way the advantage of the (additionally) covalent bonding that can take place via the quinone on suitable partners in the region of the target structure, can be particularly conveniently utilised.

A method according to the invention is preferred which the cell structure is selected from the group consisting of cells, proteins, nucleic acid, viruses, hormones, oligosaccharides, polysaccharides and bio-polymers.

Particularly preferred is a method according to the invention in which the compound V includes a signal domain.

A signal domain in the context of the present invention is a region that can serve, in conjunction with a suitable signal determination method, for the purposes of coating, quantifying or using a marking of the target structure.

It is preferred in this connection that the signal domain includes a functionality selected from the group fluorophore, chromophore, chemoluminescence partner, radioactive isotope (para)magnetic bead, nanoparticle, enzyme for detection reaction, activated sensor surface and affinity domain (for example antigen sequences, biotin, His-tag).

Preferred methods in which the signal function can be used are cell markings (FACS—fluorescence-activated cell sorting), cell labelling, labelling with coloured pigments, specific markings in vitro and in vivo, for example with tumour markers for imaging methods.

Also preferred is a method according to the invention in which the compound V has an additional function domain with biological and/or physical activity.

In this way it is also possible to couple a specific marking with a function resolution in the target structure. Thus, it is for example possible to coat certain cell types that are characterised by their specific antigens on their surfaces, with corresponding functions.

In this connection "biological activity" of the function domain is understood to mean that the compound V includes a region that influences the behaviour of a cell (e.g. via integrins) or a metabolic pathway of a cell, e.g. by blocking, activation or acceleration.

"Physical activity" means in this connection that the additional function domain of the target structure mediates an altered behaviour as regards physical phenomena such as for example fluorescence, phosphorescence, magnetism or reaction to electrical stimuli.

In this context it is preferred that the function domain is selected from the group consisting of apoptosis signal molecule, transcription factor, DNA, adjuvant, effector for signal transduction, receptor agonist or antagonist, competitive receptor effector or blocker, and also combinations of these functionalities.

Thus it is possible, in addition to this specific marking of the target structure, to achieve (further desired) effects in the target structure or on the target structure. Thus, it is for example conceivable to provide a cell specifically with an apoptosis signal after the specific marking has taken place.

Particularly preferred is a method according to the invention in which the oxidation of the dihydroxy- or trihydroxyphenyl group of the compound V to the quinone group is effected by a laccase. Laccases operate under very mild (if necessary cell-protecting) conditions, reliably and quickly actuate the activation step from the di-/triphenol to the quinone, and are sufficiently stable in many environments.

A particular effect of the method according to the invention is the possibility of obtaining/isolating special cell types from a cell mixture, in which these can be marked and subsequently selected with the aid of a compound V that is specific for them.

Examples of specific applications of the method according to the invention are described hereinafter:

Thus, it is possible to mark antibodies with a reagent comprising a marking molecule with L-DOPA and an enzyme to be used according to the invention. Since it is possible to use very specific enzymes that do not catalyse further reactions, and also no toxic substance is used, the marked antibodies can be used directly without further purification. Particularly preferred areas of application in this connection are IVD (in vitro diagnostics), marking of cells, rapid labelling with radionuclides, and in vivo imaging.

It is also possible for example to use the system for the binding of peptides: L-DOPA and other diphenols can, like amino acids, be incorporated in the synthesis of the peptides. After the activation according to the invention (oxidation of the dihydroxyphenyl group to the quinone) the thus prepared peptides form a covalent bond rapidly and irreversibly with for example amines in the next environment of their (specific) binding partner, more specifically their specific binding site (i.e. the region on the target structure that is complementary or otherwise reactive to the binding domain). This is preferably a structure on the target structure.

The method according to the invention has proved particularly suitable for covalent marking of cells (or their cell surfaces). Thus it is possible to use molecules (or binding domains) which, despite having a high specificity for a certain target molecule, would however on account of a high dissociation rate easily be removed again when washing such a preparation, or if too high a concentration of the marking compound were used would produce too high a background signal of the unbound molecule.

Reference is also made to the following example, in which the coupling of a DOPA- and fluorescein-marked peptide could be detected after enzymatic activation on cell surfaces and subsequent FACS analysis or analysis under a fluorescence microscope. The activation and marking process took only a few minutes in the experiments. It is particularly advantageous that the marking is not replaced again, which can be demonstrated by the stability of the marked cells also in the presence of non-marked cells.

Furthermore the present method according to the invention can serve as a gentle alternative to the marking and subsequent affinity purification and identification of bound proteins, for example using mass spectroscopy.

Methods for which the method according to the invention has proved to be a suitable alternative include the ProxiMol method and a method that is disclosed according to WO 2004/064972 A9, in which a non-physiological UV irradiation is necessary for the coupling.

EXAMPLES

Example 1

Marking of integrin $\alpha_v\beta_6$ expressing cells:
Materials
Cell type: Cell lines HT1299 (lung tumor), HUVEC, SVEC
Polypeptide for the marking: Ac-SPRGDLAVLGHK(FITC)GG-DOPA-G, SEQ ID NO: 1
(1-letter code for peptides; FITC: chromophore, fluorescein, excitation wavelength 490 nm, emission wavelength 520 nm)
Polypeptide solution: 4 mg/ml polypeptide in water corresponding to 2 mM
20 mg/ml laccase from Trameters versicolor, 20 U/mg, ASA Spezialenzyme GmbH, Wolfenbüttel
NaAc solution, 3 M, pH 5.6
All FAC measurements were made on a Cytomics FC500 (Beckman Coulter).
Preparation of the Test Batches:

The cells were in each case washed twice with PBS and then taken up in an amount of ca. $10^5$ cells/ml in PBS. 950 µl portions of the solution were added to 1-ml-FACS-test tubes. Marked polypeptides with and without prior treatment with laccase, were then added according to the following Table 1.

For this, 40 µl NaAc solution, 105 µl water, 15 µl peptide solution and 120 µl laccase were added in a typical 5 µm polypeptide batch. Samples without laccase contained the corresponding additional volume of water, samples with other polypeptide concentrations contained correspondingly more polypeptide solution (cf. Example 2). After an incubation time of 1 minute 50 µl were added in each case to the cell suspensions or placed in the FACS test tubes.

After an incubation time of at least 15 minutes the cells were washed three times with 2 ml PBS in the test tube and the fluorescence of the cells was then measured on a cell sorter. The total fluorescence of the cells was measured. A selection of certain cell types did not significantly alter the overall results.
Experimental batches for the background binding:

TABLE 1

| Experiment | Cell type | Description |
|---|---|---|
| 99-K0 | HT1299 | Only PBS (control without laccase) |
| 99-K5 | HT1299 | PBS with 5 µM polypeptide (control without laccase) |
| 99-5 | HT1299 | 5 µM Polypeptide with laccase |
| SV-K0 | SVEC | Only PBS (control without laccase) |
| SV-K5 | SVEC | PBS with 5 µM polypeptide (control without laccase) |
| SV-5 | SVEC | 5 µM Polypeptide with laccase |

Figure 1:
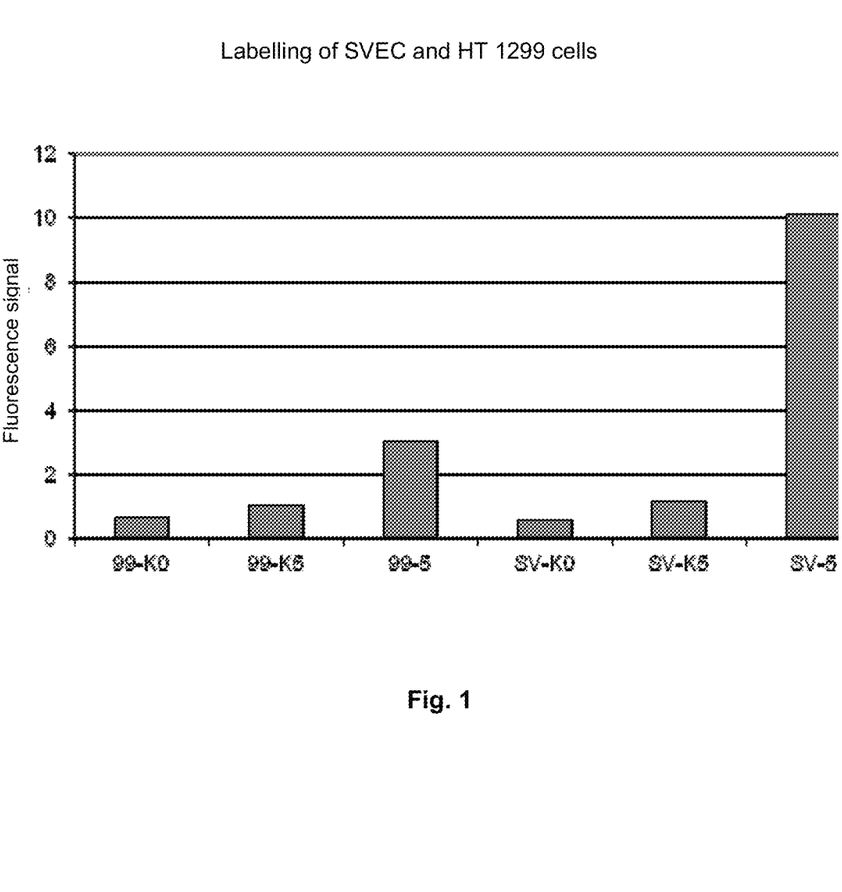
FIG. 1 shows graphically the fluorescence of washed SVEC and HT 1299 cells made according to the invention.

Result:
The results are given in FIG. 1 and show:
Without addition of laccase the polypeptide can be washed again from the cells.

Example 2

Experimental Batches for the Dependence of the Binding on the Polypeptide Concentration Corresponding to the above experimental procedure (Example 1) various cell lines, all of which express $\alpha_v\beta_6$ integrin, were marked with different polypeptide concentrations.

Figure 2:
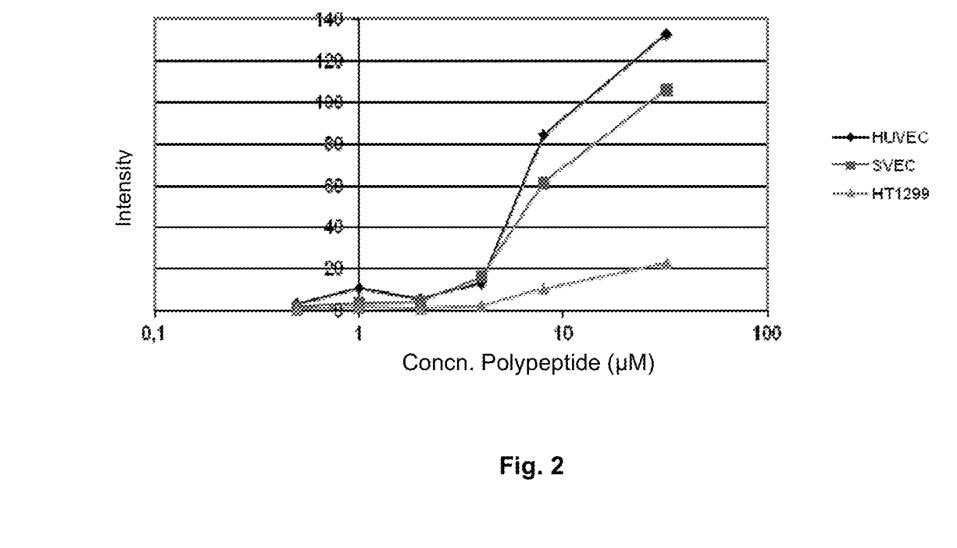
FIG. 2 shows graphically intensity values reflecting the binding of HUVEC, SVEC and HT 1229 cells as a function of polypeptide concentration.

Result:
The results are shown in FIG. 2:
The polypeptides bind depending on the concentration, in other words they exhibit a true binding curve although they were irreversibly (covalently) bonded. This means on the one hand that the oxidised biphenolic group reacts quickly when the polypeptide is (specifically) bound, and on the other hand that this group does not react so quickly that arbitrary amino groups are marked.
Overall Evaluation It is possible in practice to carry out a marking in situ, in which the oxidising enzyme (in this case laccase), the compound V (in this case the polypeptide) as well as the target structure to be marked (in this case on different cell types) are added to a reaction vessel. It has been found however that a short pre-incubation, for example of one minute, of the laccase with the polypeptide (for the activation) has an advantageous effect on the marking efficiency. This could possibly also be applied to parallel batches in the context of the invention. The conditions chosen here with a slightly acidic pH were preferably selected in order to work close to the optimum efficiency of the enzyme. From practical measurements with substrates it is known however that significantly lower enzyme concentrations and also a pH in the neutral range are sufficient.

Example 3

Coupling of Structures with DOPA Residue to a Protein

The following solutions were prepared in 10 mM phosphate buffer pH 7.0:
a) Albumen lysozyme 1 mg/ml, corresponding to 70 µM (solution 1)
b) Compound A (biotin-DOPA) 1 mg in 3 mL, corresponding to 700 µM (solution 2) and a 70 µM dilution (solution 3)
c) Compound B (biotin-RGD-DOPA) 1,2 mg in 2 ml, corresponding to 700 µM (solution 4) and a 70 µM dilution (solution 5)
d) Laccase (Trametes vers., ASA Spezialenzyme GmbH) 1 mg/ml corresponding to 20 u/ml (solution 6)

Compound A

Empirical formula=$C_{19}H_{26}N_4O_5S$
Molecular weight=422.4997 g/mol

Compound B

Empirical formula=$C_{35}H_{51}N_{11}O_{13}S$
Molecular weight=865.9118 g/mol

The reaction was started by mixing 500 µl lysozyme solution (Solution 1) with in each case 500 µl of solution 2 to solution 5 (i.e. in each case equimolar and ten-fold excess) and addition and mixing in 10 µl/0.2 u laccase (solution 6). Lysozyme with 500 µl 10 mM phosphate buffer pH 7.0 and laccase (solution 6) was used as control. The samples were incubated overnight at room temperature and the next day an aliquot was freed from low molecular weight constituents and salts using a desalting column (Micro Bio-Spin P6, BioRad) equilibrated with deionised waters.

The thereby prepared reaction product was analysed in an AB Sciex TOF/TOF™ 5800 system.

Figure 3:
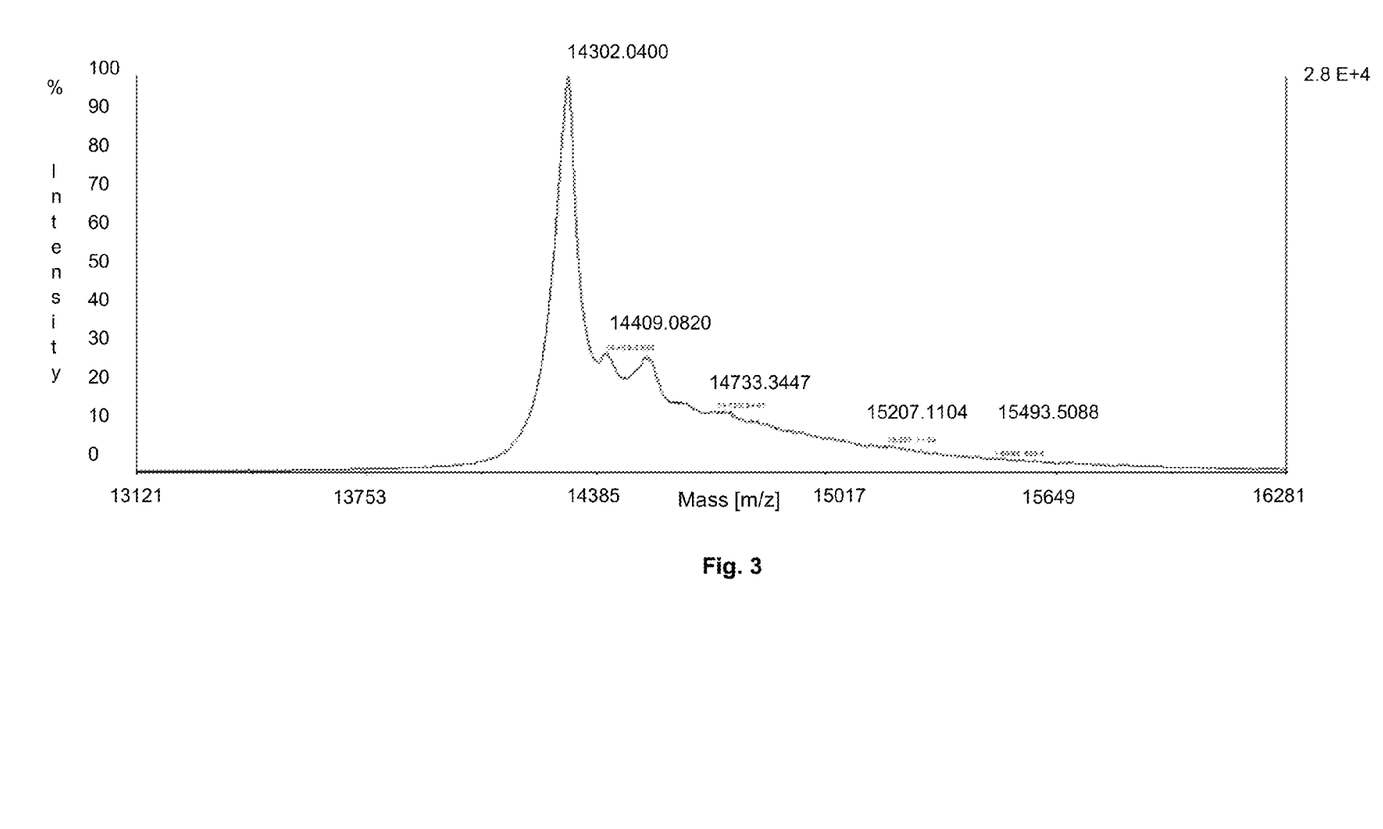
FIG. 3 shows graphically the MS analysis of the reaction of a compound A with lysozyme based on a control protein.
Figure 4:
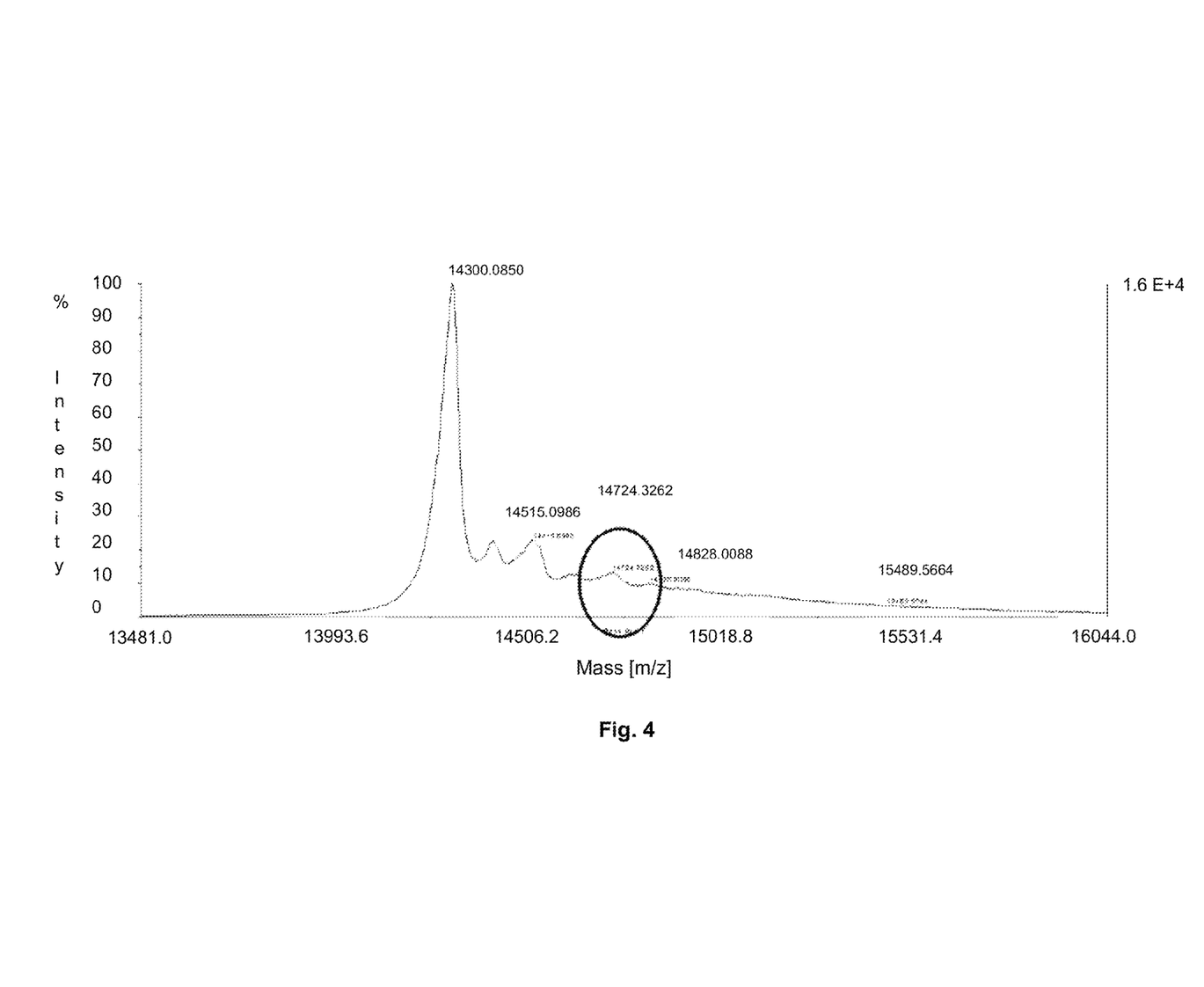
FIG. 4 shows graphically the MS analysis of the reaction of a compound A with lysozyme based on equimolar excess.
Figure 5:
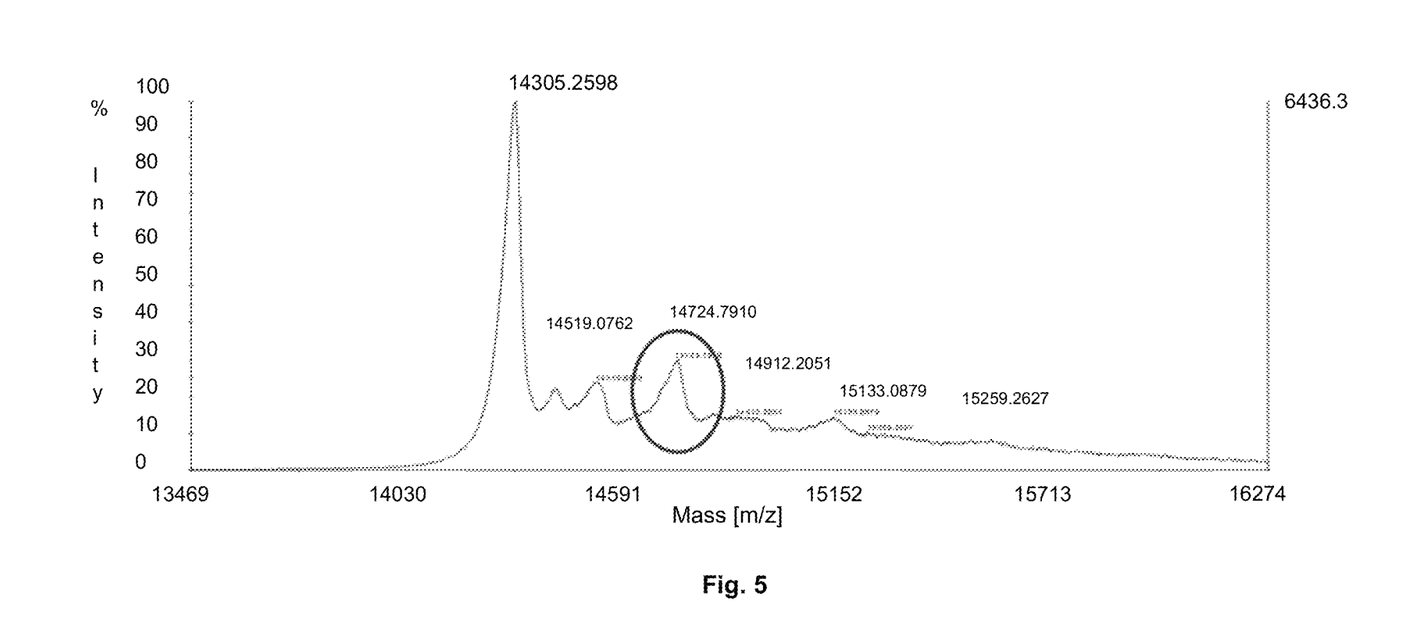
FIG. 5 shows graphically the MS analysis of the reaction of a compound A with lysozyme based on a ten-fold excess.

FIGS. 3 to 5 show: MS analysis of the reaction of compound A with lysozyme; FIG. 3 control protein, FIG. 4 equimolar excess and FIG. 5 ten-fold excess. The observed masses for the lysozome and adduct of 14300 Da to 14724.3 Da (b) and 14302 Da to 14724.8 Da (c) agree with the expected increase of 418.5 Da.

Figure 6:
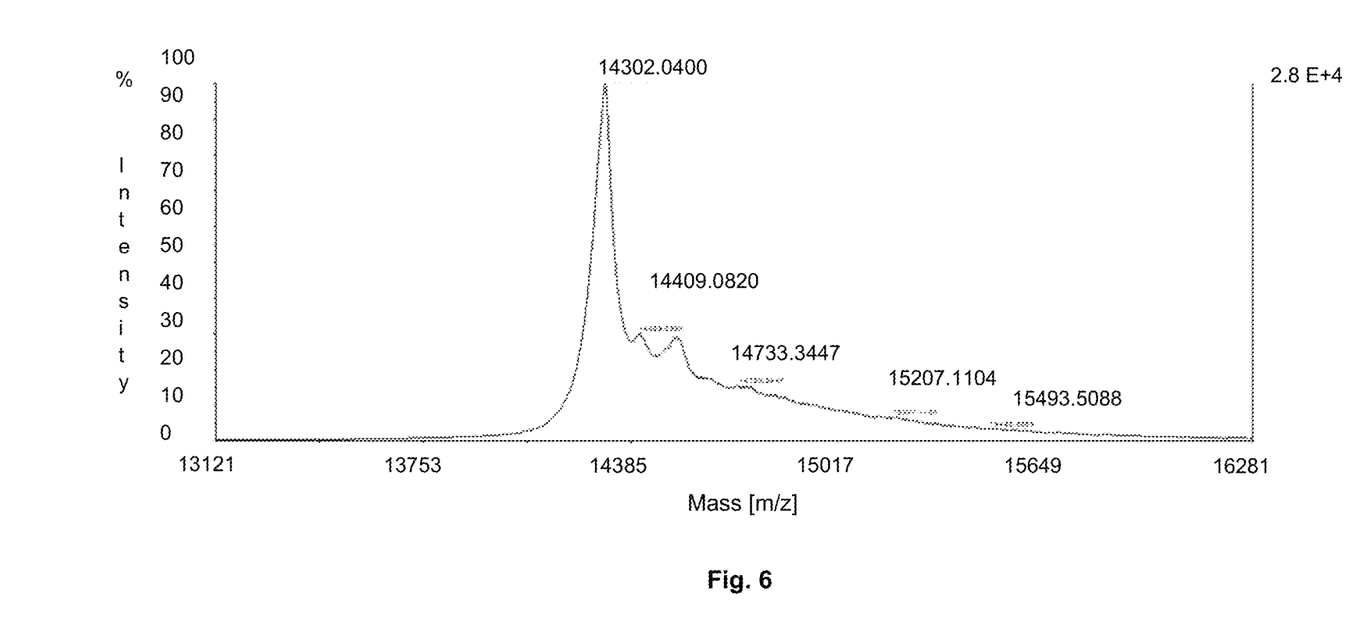
FIG. 6 shows graphically the MS analysis of the reaction of a compound B with lysozyme based on a control protein.
Figure 7:
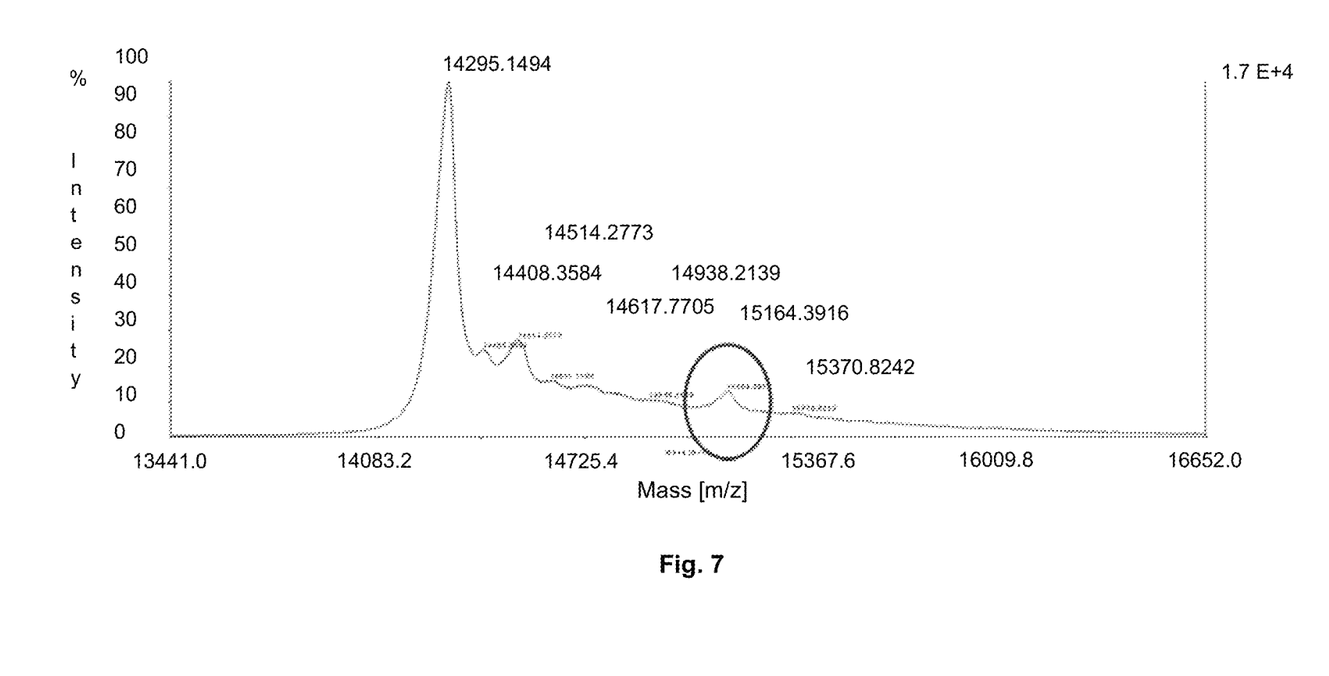
FIG. 7 shows graphically the MS analysis of the reaction of a compound B with lysozyme based on equimolar excess.
Figure 8:
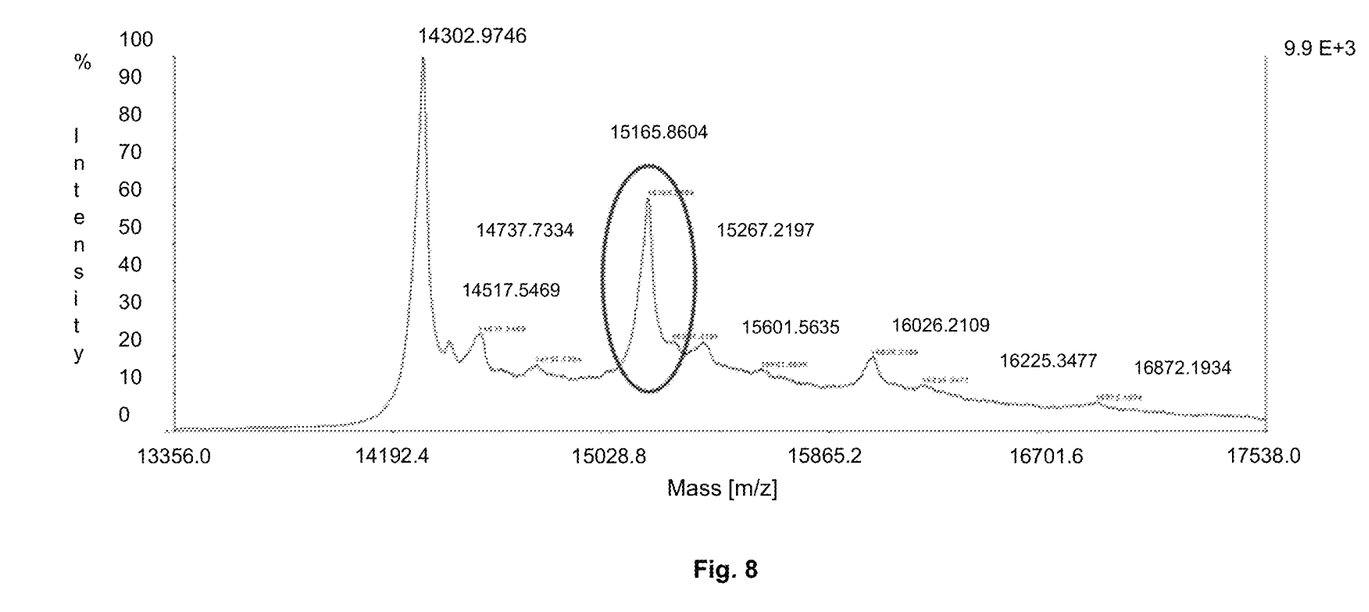
FIG. 8 shows graphically the MS analysis of the reaction of a compound Bs with lysozyme based on a ten-fold excess.

FIGS. 6 to 8 show: MS analysis of the reaction of compound B with lysozyme; FIG. 6 control protein, FIG. 7 equimolar excess and FIG. 8 ten-fold excess. The observed masses for the lysozyme and adduct of 14295 Da to 15164.4 Da (b) and 14302 Da to 15167.9 Da (c) agree with the expected increase of 861.9 Da.

The expected reaction products were found in all cases and the mass spectra (FIGS. 5 and 8) show that even with an excess of the DOPA compounds A and B a complete conversion was not achieved. Lysozyme is scarcely doubly marked even with a ten-fold excess of the DOPA compound.

CONCLUSIONS

1. The reaction takes place as expected.
2. The data confirm the founded assumption that the laccase-activated compound even in excess does not react disproportionately rapidly and completely with the protein. This also explains the possibility of an improved reaction in the case of specifically binding peptides, in the example of the integrin-binding peptide in Examples 1 and 2.

The invention claimed is:

1. A method for marking a target structure, comprising the following steps:
    a) providing a compound V that includes at least one dihydroxy- or trihydroxyphenyl group,
    b) providing an enzyme for converting the dihydroxy- or trihydroxyphenyl group to a quinone group,
    c) providing the target structure being a biological target structure,
    d) oxidizing with said enzyme the dihydroxy- or trihydroxyphenyl group of the compound V to the quinone group, and
    e) contacting the compound V with the biological target structure for marking thereof, so that a covalent bond can be formed,
        wherein in step e) the compound V is used in a concentration such that the maximum concentration of dihydroxy-, trihydroxyphenyl groups and quinone groups that were introduced by the compound V is ≤500 μM, preferably ≤300 μM, and more preferably ≤100 μM.

2. The method as claimed in claim 1, wherein the at least one dihydroxy- or trihydroxyphenyl group is a constituent of DOPA, dopamine, caffeic acid or a corresponding bound group of one of these compounds.

3. The method as claimed in claim 2, wherein:
    the compound V has precisely one dihydroxy- or trihydroxyphenyl group;
    the compound V has in addition specific binding properties for the target structure or parts of the target structure, preferably in the form of a specific binding domain;
    the specific binding properties are intended for the non-covalent bonding to the target structure;
    the target structure is selected from the group consisting of a cell, protein, nucleic acid, virus, hormone, oligosaccharide, polysaccharide and bio-polymer;
    the compound V includes an additional signal-emitting structure;
    the signal-emitting structure is selected from the group fluorophore, chromophore, chemoluminescence partner, radioactive isotope, magnetic bead, activated sensor surface, enzyme for reaction detection, activated sensor surface and affinity domain;
    the compound V has an additional function domain with biological and/or physical activity;
    the function domain is selected from the group consisting of apoptosis signal molecule, transcription factor, DNA, adjuvant, effector for signal transduction, receptor agonist, receptor antagonist, competitive receptor-effector or blocker, and also combinations of these functionalities; and
    the oxidation of the dihydroxy- or trihydroxyphenyl group of the compound V to the quinone group is effected by a laccase.

4. The method as claimed in claim 1, wherein the compound V has precisely one dihydroxy- or trihydroxyphenyl group.

5. The method as claimed in claim 1, wherein the compound V has in addition specific binding properties for the target structure or parts of the target structure, preferably in the form of a specific binding domain.

6. The method as claimed in claim 5, wherein the specific binding properties are intended for the non-covalent bonding to the target structure.

7. The method as claimed in claim 1, wherein the target structure is selected from the group consisting of a cell, protein, nucleic acid, virus, hormone, oligosaccharide, polysaccharide and bio-polymer.

8. The method as claimed in claim 1, wherein the compound V includes an additional signal-emitting structure.

9. The method as claimed in claim 8, wherein the signal-emitting structure is selected from the group consisting of fluorophore, chromophore, chemoluminescence partner, radioactive isotope, magnetic bead, activated sensor surface, enzyme for reaction detection, activated sensor surface and affinity domain.

10. The method as claimed in claim 1, wherein the compound V has an additional function domain with biological and/or physical activity.

11. The method as claimed in claim 10, wherein the function domain is selected from the group consisting of apoptosis signal molecule, transcription factor, DNA, adjuvant, effector for signal transduction, receptor agonist, receptor antagonist, competitive receptor-effector or blocker, and also combinations of these functionalities.

12. The method as claimed in claim 1, wherein the oxidation of the dihydroxy- or trihydroxyphenyl group of the compound V to the quinone group is effected by a laccase.

13. The method of claim 1, wherein the enzyme is an oxidoreductase.

14. The method of claim 13, wherein the enzyme is a laccase.

* * * * *